(12) United States Patent
Blazevic

(10) Patent No.: US 9,672,419 B2
(45) Date of Patent: *Jun. 6, 2017

(54) DETECTION OF SPURIOUS INFORMATION OR DEFECTS ON PLAYING CARD BACKS

(71) Applicant: Mladen Blazevic, New York, NY (US)

(72) Inventor: Mladen Blazevic, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/841,763

(22) Filed: Sep. 1, 2015

(65) Prior Publication Data

US 2015/0373284 A1    Dec. 24, 2015

Related U.S. Application Data

(63) Continuation-in-part of application No. 13/899,768, filed on May 22, 2013, now Pat. No. 9,316,597.

(51) Int. Cl.

| | |
|---|---|
| *H04N 7/18* | (2006.01) |
| *G06K 9/00* | (2006.01) |
| *G07F 17/32* | (2006.01) |
| *G06T 7/00* | (2017.01) |
| *A63F 1/12* | (2006.01) |
| *A63F 1/14* | (2006.01) |
| *G01N 21/88* | (2006.01) |
| *G01N 21/95* | (2006.01) |

(Continued)

(52) U.S. Cl.
CPC ........... *G06K 9/00442* (2013.01); *A63F 1/12* (2013.01); *A63F 1/14* (2013.01); *A63F 1/18* (2013.01); *G01N 21/8806* (2013.01); *G01N 21/95* (2013.01); *G06T 7/0002* (2013.01); *G07F 17/3241* (2013.01); *A63F 2009/2445* (2013.01); *A63F 2250/58* (2013.01); *G01N 2021/8816* (2013.01); *G01N 2021/8845* (2013.01); *G01N 2201/0221* (2013.01); *H04N 5/33* (2013.01)

(58) Field of Classification Search
CPC .......... G06K 9/00442; G01N 21/8806; G01N 2021/8845; G06T 7/0002; G07F 17/3241
See application file for complete search history.

(56) References Cited

U.S. PATENT DOCUMENTS

| | | |
|---|---|---|
| 4,531,187 A | 7/1985 | Uhland |
| 5,169,155 A | 12/1992 | Soules et al. |

(Continued)

FOREIGN PATENT DOCUMENTS

| | | |
|---|---|---|
| WO | WO 00/51076 | 8/2000 |

*Primary Examiner* — Christopher Findley
(74) *Attorney, Agent, or Firm* — Mark Litman & Associates, P.A.

(57) ABSTRACT

Methods and systems detect markings or flaws on the backs of playing cards. The method includes: providing ambient radiation at a gaming table and reflecting some of that radiation off a back surface of a playing card; capturing reflected radiation with a radiation sensor; the radiation sensor transmitting signals based on the reflected radiation captured by the radiation sensor; the transmitted signals providing data that contains image data of the back of the playing card; and displaying an image of the back of the playing card based on the image data. The transmitted signals provide image data of the back of the playing card and are also received by a processor that evaluates or compares that data. The system may be an installed casino system (with eye-in-the-sky technology), a portable box, or a component within a shuffling device or dealer shoe.

20 Claims, 5 Drawing Sheets

(51) Int. Cl.
*A63F 1/18* (2006.01)
*H04N 5/33* (2006.01)
*A63F 9/24* (2006.01)

(56) References Cited

U.S. PATENT DOCUMENTS

| | | |
|---|---|---|
| 5,605,334 A | 2/1997 | Mccrea, Jr. |
| 5,722,893 A | 3/1998 | Hill |
| 5,770,533 A | 6/1998 | Franchi |
| 5,941,769 A | 8/1999 | Order |
| 6,039,650 A | 3/2000 | Hill |
| 6,093,103 A | 7/2000 | Mccrea, Jr. |
| 6,117,012 A | 9/2000 | Mccrea, Jr. |
| 6,403,908 B2 | 6/2002 | Stardust et al. |
| 6,460,848 B1 | 10/2002 | Soltys et al. |
| 6,517,435 B2 | 2/2003 | Soltys |
| 6,517,436 B2 | 2/2003 | Soltys et al. |
| 6,520,857 B2 | 2/2003 | Soltys et al. |
| 6,527,191 B1 | 3/2003 | Jannersten |
| 6,527,271 B2 | 3/2003 | Soltys et al. |
| 6,530,836 B2 | 3/2003 | Soltys et al. |
| 6,530,837 B2 | 3/2003 | Soltys et al. |
| 6,533,276 B2 | 3/2003 | Soltys et al. |
| 6,533,662 B2 | 3/2003 | Soltys et al. |
| 6,579,180 B2 | 6/2003 | Soltys et al. |
| 6,579,181 B2 | 6/2003 | Soltys et al. |
| 6,582,301 B2 | 6/2003 | Hill |
| 6,588,750 B1 | 7/2003 | Grauzer et al. |
| 6,595,857 B2 | 7/2003 | Soltys et al. |
| 6,629,894 B1 | 10/2003 | Purton |
| 6,638,161 B2 | 10/2003 | Soltys et al. |
| 6,651,981 B2 | 11/2003 | Grauzer et al. |
| 6,651,982 B2 | 11/2003 | Grauzer et al. |
| 6,652,379 B2 | 11/2003 | Soltys et al. |
| 6,655,684 B2 | 12/2003 | Grauzer et al. |
| 6,659,461 B2 | 12/2003 | Yoseloff |
| 6,663,490 B2 | 12/2003 | Soltys et al. |
| 6,676,127 B2 | 1/2004 | Johnson |
| 6,685,568 B2 | 2/2004 | Soltys et al. |
| 6,688,979 B2 | 2/2004 | Soltys et al. |
| 6,712,696 B2 | 3/2004 | Soltys et al. |
| 6,726,205 B1 | 4/2004 | Purton |
| 7,338,044 B2 | 3/2008 | Grauzer et al. |
| 7,367,561 B2 | 5/2008 | Blaha et al. |
| 7,367,884 B2 | 5/2008 | Breeding et al. |
| 7,374,170 B2 | 5/2008 | Grauzer et al. |
| 7,384,044 B2 | 6/2008 | Grauzer et al. |
| 7,407,438 B2 | 8/2008 | Schubert et al. |
| 7,413,191 B2 | 8/2008 | Grauzer et al. |
| 7,434,805 B2 | 10/2008 | Grauzer et al. |
| 7,584,962 B2 | 9/2009 | Breeding et al. |
| 7,584,963 B2 | 9/2009 | Krenn et al. |
| 7,593,544 B2 | 9/2009 | Downs, III et al. |
| 7,594,660 B2 | 9/2009 | Baker et al. |
| 7,597,623 B2 | 10/2009 | Grauzer et al. |
| 7,669,852 B2 | 3/2010 | Baker et al. |
| 7,677,565 B2 | 3/2010 | Grauzer et al. |
| 7,677,566 B2 | 3/2010 | Krenn |
| 7,699,694 B2 | 4/2010 | Hill |
| 7,717,427 B2 | 5/2010 | Grauzer et al. |
| 7,753,373 B2 | 7/2010 | Grauzer et al. |
| 7,764,836 B2 | 7/2010 | Downs, III et al. |
| 7,769,232 B2 | 8/2010 | Downs, III |
| 7,784,790 B2 | 8/2010 | Grauzer et al. |
| 7,854,430 B2 | 12/2010 | Toyama |
| 7,933,444 B2 | 4/2011 | Downs, III et al. |
| 7,933,448 B2 | 4/2011 | Downs, III |
| 7,946,586 B2 | 5/2011 | Krenn et al. |
| 7,950,663 B2 | 5/2011 | Schubert et al. |
| 7,967,294 B2 | 6/2011 | Blaha et al. |
| 7,967,672 B2 | 6/2011 | Shigeta |
| 7,971,881 B2 | 7/2011 | Toyama et al. |
| 7,976,023 B1 | 7/2011 | Hessing |
| 7,988,152 B2 | 8/2011 | Sines |
| 8,002,638 B2 | 8/2011 | Grauzer et al. |
| 8,011,661 B2 | 9/2011 | Stasson |
| 8,012,029 B2 | 9/2011 | Johnson |
| 8,020,869 B2 | 9/2011 | Kaji et al. |
| 8,025,294 B2 | 9/2011 | Grauzer et al. |
| 8,038,521 B2 | 10/2011 | Grauzer et al. |
| RE42,944 E | 11/2011 | Blaha et al. |
| 8,070,574 B2 | 12/2011 | Grauzer et al. |
| 8,109,514 B2 | 2/2012 | Toyama |
| 8,118,305 B2 | 2/2012 | Grauzer et al. |
| 8,150,875 B1 | 4/2012 | Dubrovsky et al. |
| 8,170,323 B2 | 5/2012 | Downs, III |
| 8,191,894 B2 | 6/2012 | Grauzer et al. |
| 8,205,884 B2 | 6/2012 | Schubert et al. |
| 8,210,535 B2 | 7/2012 | Grauzer et al. |
| 8,210,536 B2 | 7/2012 | Blaha |
| 8,221,244 B2 | 7/2012 | French |
| 8,969,802 B1 * | 3/2015 | Blazevic .................. A63F 1/12 250/330 |
| 9,316,597 B2 * | 4/2016 | Blazevic .................. A63F 1/12 |
| 2004/0026636 A1 | 2/2004 | Shigeta |
| 2005/0156046 A1 | 7/2005 | Goldenberg et al. |
| 2005/0242500 A1 | 11/2005 | Downs, III |
| 2007/0018389 A1 | 1/2007 | Downs, III |
| 2007/0102879 A1 | 5/2007 | Stasson |
| 2009/0291758 A1 | 11/2009 | Moretti |
| 2010/0019449 A1 | 1/2010 | Downs, III et al. |
| 2010/0061342 A1 | 3/2010 | Frederiks et al. |
| 2011/0020175 A1 | 1/2011 | Collard et al. |
| 2011/0227283 A1 | 9/2011 | Schubert |
| 2013/0343599 A1 | 12/2013 | Lee et al. |

* cited by examiner

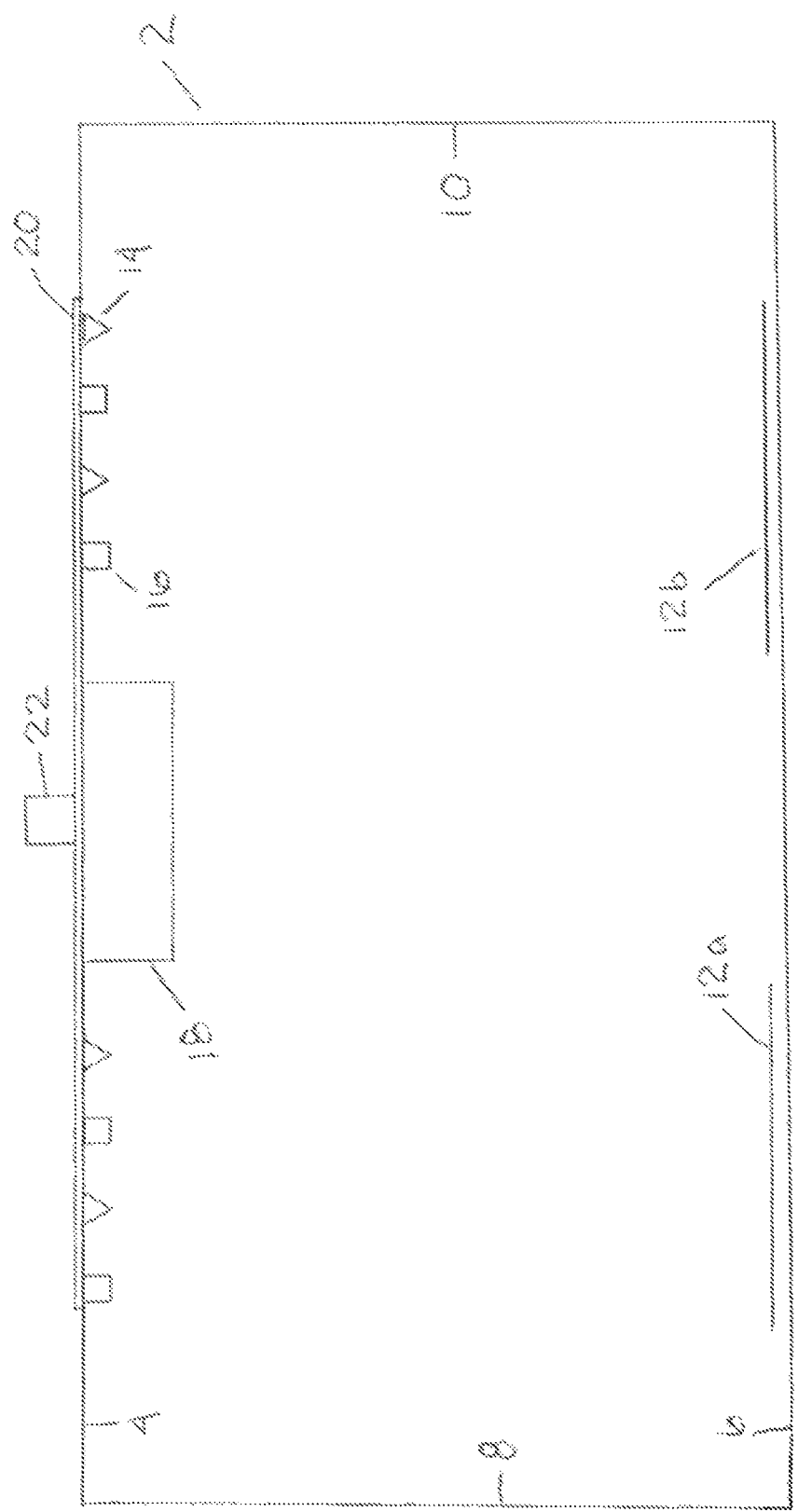

FIGURE 2

A method for detecting errors in the back of playing cards by:

- Provide ambient infrared radiation at a gaming table and reflecting at least some of that infrared radiation off a back surface of a playing card

↓

- Capture reflected infrared radiation with an infrared radiation sensor

↓

- The infrared radiation sensor transmits signals based on the reflected infrared radiation captured by the infrared radiation sensor

↓

- The transmitted signals provide data that contains image data of the back of the playing card; and

↓

- A display system displays an image of the back of the playing card based on the image data.

FIGURE 3

A method for detecting errors in the back of playing cards by:

Provide ambient infrared, ultraviolet and visible radiation within a housing at a gaming table and reflecting at least some of that radiation off a back surface of a playing card;

↓

Capture reflected radiation with a radiation sensor;

↓

The radiation sensor transmits signals based on the reflected radiation captured by the radiation sensor;

↓

The transmitted signals provide data that contains image data of the back of the playing card;

↓

Images of the playing cards from each of the transmitted signals of ultraviolet, infrared and visible radiation are either separately displayed, displayed in subsets or viewed contemporaneously; and

↓

A display system displays an image of the back of the playing card based on the image data.

DETECTION OF SPURIOUS INFORMATION OR DEFECTS ON PLAYING CARD BACKS

RELATED APPLICATIONS DATA

The present application claims priority under 35 U.S.C. 120 as a continuation-in-part application from U.S. patent application Ser. No. 13/899,768, filed 22 May 2013.

BACKGROUND OF THE INVENTION

Field of the Invention

The present invention relates to the field of playing cards, particularly playing cards used in wagering games, and more particularly to the security of playing cards with respect to spurious information and defects on the back surfaces of playing cards.

Background of the Art

Even with the highly electronic advances that have occurred within the gaming industry, playing cards, dice and other physical gaming objects are still important implements within gaming venues. Playing cards in particular are suspect of and capable of manipulation by players because of the intimate and repeated contact with the playing cards by the players.

Card games and card tournaments can involve millions of dollars in individual and total prizes. Some players have attempted to mark playing cards on the backs or edges of cards so that the markings enable them to identify the suit and rank of cards without having the faces of the cards exposed. This provides a significant advantage to players involved in fraudulent marking of playing cards versus other players or the house. Even though marking has been going on for over a hundred years, and even though cards are visually inspected by dealers and automated systems can inspect or read values of playing cards, newer techniques and more sophisticated markings or defects can still go undetected. New types of markings are invisible to the naked eye, but can be clearly seen with the help of specially made contact lenses and glasses and small portable cameras with built in video transmitters. Small CPUs in pockets may be used to transfer the information to the player via wireless, inductive earphone. The marked cards (packaged in original boxes and sealed), chemicals and cheating devices are being widely sold over Internet for the last couple of years. As recently as May 2013, an international professional poker player was accused of cheating (and winning over 10 million dollars) in a major tournament by reading variations in printed patterns on the backs of playing cards. This is asserted to have occurred in spite of the casino supplying and controlling the cards, regular change of decks of cards, and constant dealer examination of the cards. Because there is a wide range of types of markings, inspections of card backs is usually effective for only single types of markings.

The types of markings that can be provided on backs and sides of playing cards include at least, visible ink, invisible inks (e.g., infrared and/or ultraviolet reflecting ink), solvents that smear existing inks, abrading or cutting marks, matting agents that alter reflectivity of surfaces, bending or curling of cards, and the like, alone or in combinations. Manual inspection can be done visually (with or without red color glasses that enhance viewability of the one part of the visible spectrum, but markings in infrared or UV can't be detected with the naked eye), manually (feeling for abrasions or marks) and by combinations of these actions.

Many different types of automated reading, sensing and optical electrical or electromechanical systems are known for use in reading or sensing playing cards. A non-limiting sampling of those types of systems is reviewed below.

U.S. Pat. No. 6,403,908 (Stardust) discloses an automated method and apparatus for sequencing and/or inspecting decks of playing. The method and apparatus utilizes pattern recognition technology or other image comparison technology to compare one or more images of a card with memory containing known 'good' images of a complete deck of playing cards to identify each card as it passes through the apparatus. Once the card is identified, it is temporarily stored in a location corresponding to or identified according to its position in a properly sequenced deck of playing cards. Once a full set of cards has been stored, the cards are released in proper sequence to a completed deck hopper. The method and apparatus also includes an operator interface capable of displaying a magnified version of potential defects or problem areas contained on a card which then may be viewed by the operator on a monitor or screen and either accepted or rejected via operator input. The patent is also capable of providing an overall wear rating for each deck of playing cards. In order to certify that deck of playing cards is good and acceptable for play, the casino must ascertain that: (1) there is one and only one of each type (i.e. by suit and rank) of playing card in the deck of playing cards, (2) all of the backs of the playing cards contained in the deck are of the same color, (3) there are no defective playing cards (i.e. torn or cracked cards, cards with dimples or fingernail marks, cards with missing print or cards with spots), and (4) there are no boxed cards (cards facing backwards, etc.) contained in the deck of playing cards. Imaging cameras are used to obtain one or more images of each side of the card after the double card check is made. A low resolution image is made of the front to determine suit and rank and back to determine color of the card. Generally, high resolution imaging is utilized to determine fine marks and problems. If the system is not in an inspect mode, it is possible to use the cameras simply to image a corner of the card, since the information necessary as to color and suit and rank is available in this portion of each card.

U.S. Pat. No. 5,941,769 (Order) discloses that in professional use in table games of chance, playing cards are provided which will register and evaluate all phases of the run of the game automatically. This is achieved by a card shoe with an integrated device for recognition of the value of the drawn cards (optical recognition device and mirroring into a CCD-image converter); photodiodes arranged under the table cloth to register separately the casino light passing through each area for placing the gaming chips and areas for placing the playing cards in dependence of the arrangement or movement of the chips and playing cards on the mentioned areas; a device for automatic recognition of each bet (scanner or a RFID-system comprising a S/R station and gaming objects with integrated transponder); an EDP program created in accordance with the gaming rules to evaluate and store all data transmitted from the functional devices to the computer; and a monitor to display the run of the game and players' wins.

U.S. Pat. No. 5,770,533 (Franchi) describes a casino operating system for controlling the flow of funds and monitoring gambling activities in a casino or a gaming establishment utilizing a network of computers, including a central computer and individual game computers. Each player receives an encoded betting card from the cashier. At the games, each player position is equipped with a control panel including a card reader into which the betting card is inserted. The control panel also includes an electronic screen and keyboard. From the control panel, the player may place a bet and perform all options available to the player in the particular game. The system records the hands dealt to each player and the winner, and credits or debits the player's betting card accordingly. In an alternative embodiment, the casino operating system allows the players to use chips to place bets instead of the above-described betting card. The chips are marked or encoded so that they can be counted once final bets have been placed to determine the amount of each player's bet. In games requiring the placement of bets in certain positions on the gaming table, each player may be provided with a betting marker used to indicate the position of his bets on the table, a touch-sensitive screen maybe used whereby bets are placed by touching the desired position on the screen, or a two-way remote control console for placing bets. The casino operating system is an open architecture system adaptable to accommodate the differing needs of each casino.

U.S. Pat. No. 4,531,187 (Uhland) describes a system for monitoring the play at gambling games. The preferred embodiment comprises a system for monitoring the play at blackjack as that game is played in casinos. The system typically will comprise video monitor means for generating a digital representation of the bets made by the players and of the cards dealt to the players and to the dealer, so that an output can be generated indicating whether the correct payouts are made and bets collected. An alarm signal is generated if an error is made in the play of the game. An alarm signal may also be generated if the long-term statistics of the game indicate that the odds ordinarily applicable to the game have been departed from over a period of time.

U.S. Pat. No. 8,221,244 (French) describes methods and systems for intelligent tracking and/or play and/or management of card gaming use an intelligent card distribution or holding device with detectors for determining the value and unique identity of individual cards and for recording card play. Playing cards are equipped with a read/write data storage connected to a transponder and/or incorporated into electromagnetic writable particles or smart particles (smart dust). A system of the invention records various game play events on the playing cards themselves during game play and optionally also in a database on the system. In specific embodiments, the principal scanning and writing elements and electronic and optical interfaces are embodied into a hand-held card holder (HHCH). The system can scan playing cards, scan gaming chips, indicate a player's win/loss/draw, increase or decrease player betting positions, and compute awards to players based on their playing activity.

U.S. Pat. No. 7,967,672 (Shigeta) describes a card reading device that comprises a rail for guiding a card; card sensors for detecting a passing card which is slid by hand and guided by the rail, which are placed in a card sliding direction with a certain gap; and reading sensors for reading code attached to the card, which are placed between the two card sensors in the card sliding direction. The cards have the code which is printed in UV-luminous ink on the card, and the code comprises at least two code rows which are placed across the card sliding direction with a certain gap. The two reading sensors are placed in positions which correspond to the gap of the two code rows, and the card sensors output signal for detecting a position of the passing card.

U.S. Pat. No. 6,629,894 (Purton) describes a card inspection device that includes a first loading area adapted to receive one or more decks of playing cards. A drive roller is located adjacent the loading area and positioned to impinge on a card if a card were present in the loading area. The loading area has an exit through which cards are urged, one at a time, by a feed roller. A transport path extends from the loading area exit to a card accumulation area. The transport path is further defined by two pairs of transport rollers, one roller of each pair above the transport path and one roller of each pair below the transport path. A camera is located between the two pairs of transport rollers, and a processor governs the operation of a digital camera and the rollers. A printer produces a record of the device's operation based on an output of the processor, and a portion of the transport path is illuminated by one or more blue LEDs. Preferably a low temperature source of light is located so as to illuminate the area of the card that is being scanned.

The computer or signal processor compiles the scan data and reports and records the result of the scans of all of the cards in the one or more decks. FIG. 15 of Purton illustrates how a card transport path 400 may be subdivided by locating baffles above or below the roller pairs in order to create distinct zones. Each zone may have a particular form of detector, polarimeter, diode or line scanner as well as a particular light source or lighting method. By locating sensors both above and below the transport path, both sides of the card may be examined simultaneously. This provides the opportunity to detect suit and value of an inverted card as well as increasing the sophistication with which tampering may be detected. Polarized light may be used to detect certain forms of tampering. In such a case, the polarity of the light source may be rotated during the detection process. Similarly, a non-polarized source may be moved during the detection process to create a moving shadow. One or more light sources may be movable or set to illuminate off-axis so that certain forms of scratches and pinholes may be more easily detected by their shadow or reflectance. It is contemplated that both color and monochrome imaging methods may provide useful information about the condition of the cards. Similarly both digital and analogue sensing methods are seen to have independent utility and functionality with regard to both suit and value detection as well as the detection of faults, wear and tampering. It should be noted that the compartmentalization of the card transport path into distinct lighting and sensing zones may be applied to any embodiment disclosed.

Published U.S. Patent Application Document No. 20050242500 (Downs III) describes a sensing system for determining the rank and suit of playing cards. The system includes a sensing module capable of reading a line of data from a printed image, a position sensor and a hardware component that combines the signals from the sensing module and position sensor, converts the signal to binary values and compares the converted signal to stored signals. The comparisons are correlated to identify card rank and Suit. The system can be used in a playing card delivery shoe used to control the game of baccarat. The shoe may be a customary dealing shoe equipped with a sensing module, or may be a mechanized shoe. The mechanized shoe may comprise a) an area for receiving a first set of playing cards useful in the play of the casino table card game of baccarat; b) first card mover that moves playing cards from the first set to a playing card staging area wherein at least one playing card is staged in an order by which playing cards are removed from the first set of and moved to the playing card staging area; c) second playing card mover that moves playing cards from the playing card staging area to a delivery area wherein playing cards removed from the staging area to the delivery shoe are moved in the same order by which playing cards were removed from the first set of playing cards and moved to the playing card staging area; and d) playing card reading sensors that read at least one playing card value of each playing card separately after each playing card has been removed from the area for receiving the first set of playing cards and before removal from the playing card delivery area One exemplary sensing system is a CIS line scanning system with an associated card position sensor and a FPGA hardware element.

Published U.S. Patent Application Document No. 20070018389 (Downs III) describes a method and an apparatus determines at least one of rank or suit of a playing card. The apparatus has at least one two-dimensional complementary metal oxide semiconductor imaging system that provides a signal when playing cards are moved over the system. The signal is a series of gray scale values that are converted into binary values. The sensed data is transmitted to a hardware component that identifies at least one of rank and suit to an external data storage device.

Published U.S. Patent Application Document No. 20070102879 (Stasson) describes a playing card shuffling device has a visual display in information communication with the playing card shuffling device. At least one processor is programmed to provide displayable information to the visual display indicative of an amount of time remaining or time expired in a procedure performed by the shuffling device. FIG. 1 shows a partial perspective view of the top surface of a first shuffling and card verification apparatus according to a practice of the invention. In this example of the invention, the device randomizes and/or verifies one or two decks of cards. The shuffling apparatus has a card accepting/receiving area that is preferably provided with a stationary lower support surface that slopes downwardly from the nearest outer side of the shuffling and verifying apparatus. A depression is provided in that nearest outer side to facilitate an operator's ability to place or remove cards into the card accepting/receiving area. The top surface of the shuffling and verifying apparatus is provided with a visual display (e.g., LED, liquid crystal, micro monitor, semiconductor display, multi-segment display, etc.), and a series of buttons, touch pads, lights and/or displays. These elements on the top surface of the shuffling and verifying device may act to indicate power availability (on/off), shuffler state (jam, active shuffling, completed shuffling cycle, insufficient numbers of cards, missing cards, sufficient numbers of cards, complete deck(s), damaged or marked cards, entry functions for the dealer to identify the number of players, the number of cards per hand, access to fixed programming for various games, the number of decks being shuffled, card calibration information, mode of operation (i.e. shuffling, verifying or both shuffling and verifying) and the like), or other information useful to the operator or casino. Among the non-limiting examples of these techniques are 1) a sensor so that when a pre-selected portion of the card (e.g., leading edge, trailing edge, and mark or feature on the card) passes a reading device, such as an optical reader, the bottom pick-off roller is directed to disengage, revolve freely, or withdraw from the bottom of the set of cards; 2) the first set of nip rollers or off-set rollers may have a surface speed that is greater than the surface speed of the bottom pick-off roller, so that engagement of a card applies tension against the bottom pick-off roller and the roller disengages with free rolling gearing, so that no forward moving forces are applied to the first card or any other card exposed upon movement of the first card; 3) a timing sequence so that, upon movement of the bottom pick-off roller for a defined period of time or for a defined amount of rotation (which correlates into a defined distance of movement of the first card), the bottom pick-off roller disengages, withdraws, or otherwise stops applying forces against the first card and thereby avoids applying forces against any other cards exposed by movement of the first card from the card accepting/receiving area 106 and 4) providing a stepped surface (not shown) between pick-off roller and off-set rollers 146 that contacts a leading edge of each card and will cause a card to be held up or retained in the event that more than one card feeds at a time.

Shuffler systems, especially those having a scanning system, can be converted to card inspections systems or may have card inspection systems according to the present technology integrated into the shufflers, randomizers and playing card delivery systems. Examples of such card moving systems include, but are not limited to U.S. Pat. Nos. 8,210,536; 8,210,535; 8,205,884; 8,191,894; 8,170,323; 8,150,875; 8,118,305; 8,109,514; 8,070,574; RE 42,944; 8,038,521; 8,025,294; 8,012,029; 8,011,661; 8,002,638; 7,988,152; 7,976,023; 7,971,881; 7,967,294; 7,950,663; 7,946,586; 7,933,448; 7,933,444; 7,854,430; 7,784,790; 7,769,232; 7,764,836; 7,753,373; 7,717,427; 7,699,694; 7,677,566; 7,677,565; 7,669,852; 7,597,623; 7,594,660; 7,593,544; 7,584,963; 7,584,962; 7,434,805; 7,413,191; 7,407,438; 7,384,044; 7,374,170; 7,367,884; 7,367,561; 7,338,044; 6,676,127; 6,659,461; 6,655,684; 6,651,982; 6,651,981; 6,588,750; and 6,588,750.

Other disclosures have also contemplated optically reading of playing cards. For example, U.S. Pat. Nos. 6,582,301; 6,039,650; and 5,722,893 to Hill et al. describes a shoe with a card scanner, which optically scans a playing card as the card moves out of shoe. The card suit and value is then recognized by a neural-network algorithm. Other disclosures have also attempted to track cards by use of card shoes that optically recognize the cards as they are drawn from the shoe. For example, U.S. Pat. Nos. 5,941,769 and 6,460,848 disclose a card shoe with an optical device that deflects and transmits a reflected image of the card value imprint from the drawn playing card to a CCD image converter. Still other disclosures have attempted to combine detection of playing cards optically and gambling chips by some means. For example, U.S. Pat. Nos. 5,605,334; 6,093,103 and 6,117,012 to McCrea et al., disclose a game table system for monitoring each hand in a progressive live card game. The system comprises a shoe that optically detects the value and suit of each card, a game bet sensor to detect the presence or absence of a bet, a card sensor located at each player position to detect the presence or absence of a playing card, and a game control. The game control receives information on the presence or absence of a bet or playing card to ensure a bet is placed before the playing card is dealt.

Published U.S. Patent Application Document No. 20100019449 (Downs III) describes how a playing card delivery shoe is used in the play of the casino table card game of baccarat or blackjack or any game where cards are pulled one at a time from the shoe. The apparatus comprises a reader or an imager that scans lines bisecting the image at spaced intervals. The scanning occurs on playing cards in at least the region where suit and rank symbols are provided. The scanner output is a series of voltages that are converted to binary information. This binary information is compared to stored binary information to determine rank and suit. The upper surface of the output end of the shoe contains a partial barrier for cards being scanned. The partial barrier has an elevated surface and limits a size of a pathway so that only one card can be removed at a time.

U.S. Pat. No. 6,460,848 (Soltys) describes a system that automatically monitors playing and wagering of a game, including the gaming habits of players and the performance of employees. A card deck reader automatically reads a symbol from each card in a deck of cards before a first one of the cards is removed. The symbol identifies a respective rank and suit of the card. There are numerous other related patents including U.S. Pat. Nos. 6,712,696; 6,688,979; 6,685,568; 6,663,490; 6,652,379; 6,638,161; 6,595,857; 6,579,181; 6,579,180; 6,533,662; 6,533,276; 6,530,837; 6,530,836; 6,527,271; 6,520,857; 6,517,436; and 6,517,435.

U.S. Pat. No. 8,119,975 (Downs III) describes a high speed deterministic, non-contact, 3-axis free trajectory measurement device and free trajectory imaging device. A data providing device associated with a trajectory sensing system has at least a frame. The frame supports at least two sensing receivers and at least one emitter for the sensing receivers. The sensors sense movement and/or position with respect to a surface. The frame supports a third sensor that senses information (e.g., image data) from the surface at least in addition to movement. There is also a communication link from the two sensing receivers to a data storage device; a communication link from the third sensor to a data storage device or to a processor and then a data storage device; and a processor that determines position of the system with respect to the surface based at least in part on data from the two sensing receivers. The emitters and sensors may be carried on a hand-held device in communication with a recorder or processor.

Other systems known to be available for reading of card symbols (e.g., suits and rank) include at least WIPO Published Application WO/2000/051076 (Dolphin); Published U.S. Patent Application Documents No. 2011020175; 2010061342; 20040026636; and U.S. Pat. Nos. 6,726,205; 6,527,191; 6,533,276 and 8,020,869. All of the references cited herein are incorporated by reference in their entirety to provide enabling background for systems and technology and methods.

SUMMARY OF THE INVENTION

The present invention relates to the field of methods and systems for detection of spurious or fraudulent markings or flaws on the backs of playing cards. The invention includes a method and system for detecting errors on the backs of playing cards. The method includes: providing ambient infrared radiation at a gaming table and reflecting at least some of that infrared radiation off a back surface of a playing card; capturing reflected infrared radiation with an infrared radiation sensor; the infrared radiation sensor transmitting signals based on the reflected infrared radiation captured by the infrared radiation sensor; the transmitted signals providing data that contains image data of the back of the playing card; and displaying an image of the back of the playing card based on the image data. The transmitted signals provide data that contains image data of the back of the playing card and is also received by a processor that compares that transmitted data with reference data of a standard playing card back. Deviations from the reference data are recognized by the processor and identification of a card with such deviations is made. The detection system may be an installed casino system (with eye-in-the-sky technology), a portable box, a hand-held device, or a component within a shuffling device or dealer shoe.

BRIEF DESCRIPTION OF THE FIGURES

FIG. 1 shows a full frontal view of a device according to the present technology.

FIG. 2 is a flow chart for a method according to the present technology.

FIG. 3 is a flow chart for an alternative method for practice of the present technology.

DETAILED DESCRIPTION OF THE INVENTION

Figure 4:
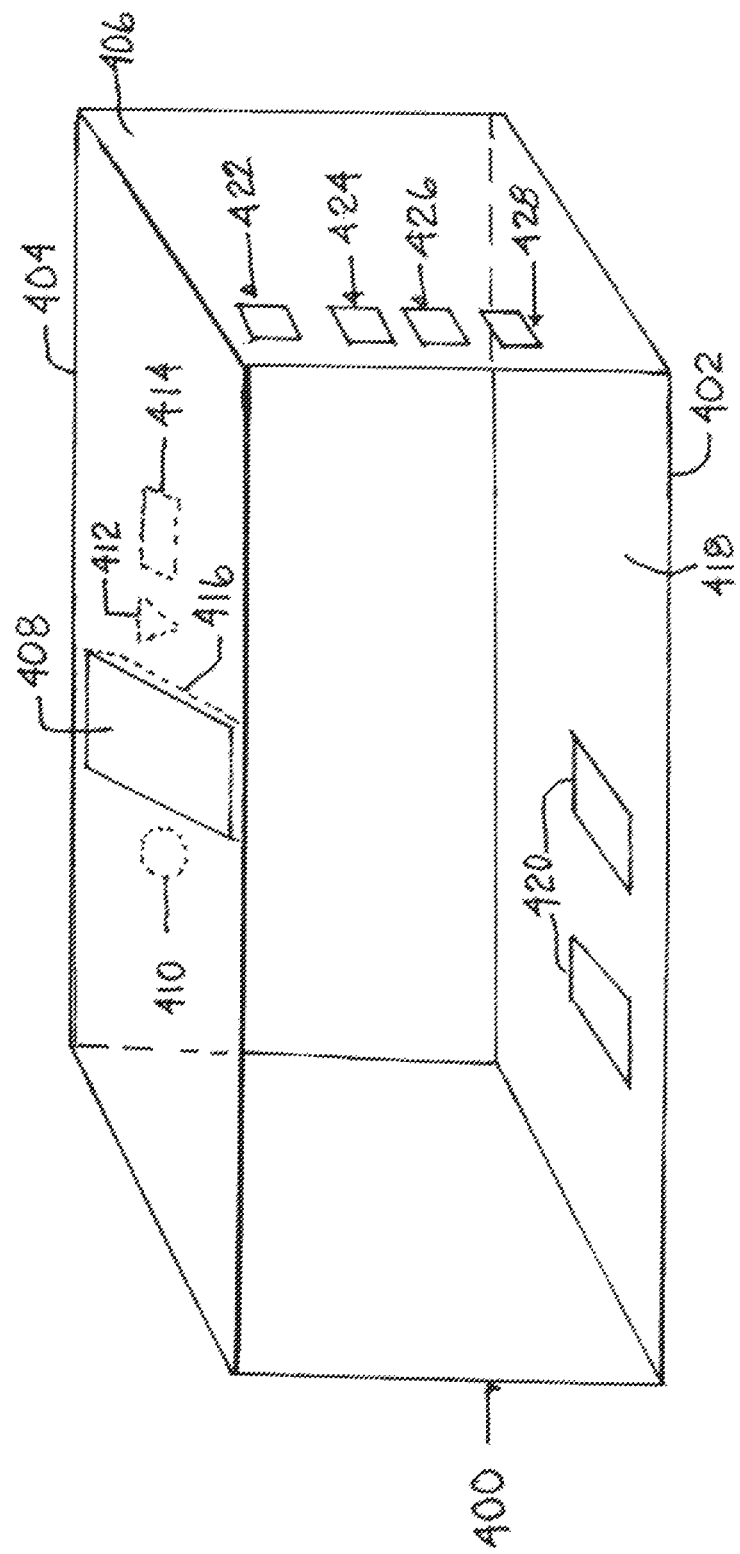
FIG. 4 shows a perspective view of an alternative device 400 according to the present technology.

The present invention relates to the field of methods and systems for detection of markings (especially spurious or fraudulent markings) or flaws on the backs or edges of playing cards. The invention includes a method for detecting errors in the back of playing cards. The method includes: providing ambient infrared radiation at a gaming table and reflecting at least some of that infrared radiation off a back surface of a playing card; capturing reflected infrared radiation with an infrared radiation sensor; the infrared radiation sensor transmitting signals based on the reflected infrared radiation captured by the infrared radiation sensor; the transmitted signals providing data that contains image data of the back of the playing card; and a processor evaluating an image of the back of the playing card based on the image data in comparison to stored or available image data of an acceptable plying card back and/or edge, or displaying an image of the back of the playing card based on the image data for visual inspection. The transmitted signals provide data that contains image data of the back of the playing card may also be received by a processor that compares that transmitted data with reference data of a standard playing card back with respect to the set of playing cards in use during a casino table playing card game. The differences between the image of the back of the playing card based on the image data and the reference data are either a) highlighted in a visual display or b) the processor identifying a degree of difference (or cards with a degree of difference) between the image of the back of the playing card based on the image data and the reference data. The degree of differences between the image of the back of the playing card based on the image data and the reference data is preferably identified by the processor in b) by an alphanumeric rating, color rating or symbolic rating. An unacceptable or questionable degree of difference may be used by the processor to alert personnel, send an alert signal, or even stop game progression while the card with the degree of difference is further inspected. The sensor may be located at a position elevated above a surface of the gaming table, or even in a hand-held device swept over card backs that might be under suspicion. For example, the sensor may be elevated to a height wherein infrared radiation reflected from the back surface of the playing card at an angle of between 60 and 90 degrees from horizontal is received by the sensor. This can be done within a housing or on a casino floor where the sensor is housed within a dome secured to a ceiling or supported on a post adjacent the table.

In a preferred method and system, in addition to the infrared radiation, the method contemporaneously (in an adjacent time frame, an overlapping time frame or the same time frame) provides ambient ultraviolet radiation at the gaming table, in a hand-held device (see Downs III U.S. Pat. No. 8,119,975 which could be modified for practice in the present technology) or in a housing and reflecting at least some of that ultraviolet radiation off the back surface of the playing card; capturing reflected ultraviolet radiation with an ultraviolet radiation sensor; the ultraviolet radiation sensor transmitting signals based on the reflected ultraviolet radiation captured by the ultraviolet radiation sensor; the transmitted signals based on the ultraviolet radiation providing data that contains image data of the back of the playing card; and a processor comparing the transmitted data to reference data of acceptable playing card backs and/or the system displaying an image of the back of the playing card based on the ultraviolet image data for visual inspection. A processor may combine the infrared and ultraviolet image data to form a single composite image of the back of the playing card. The provided ambient infrared radiation may be pulsed at the back of the playing card to reduce infrared heating of the back of the playing card.

The invention may also include a system for detecting errors in the back of playing cards comprising:
an ambient infrared radiation source for directing infrared radiation at a surface;
an infrared radiation sensor for capturing reflected ambient infrared radiation;
the infrared radiation sensor configured to transmit signals based on captured reflected infrared radiation;
the transmitted signals providing data that contains image data reflected off of the surface;
a processor configured to receive the transmitted signals, process the transmitted signals and transmit the processed transmitted signals in a format that can be displayed on a display system; and
a display system configured to display an image of the surface from which infrared radiation was reflected based on the image data.

Alternatively, steps d) and e) may be:
d) a processor configured to receive the transmitted signals, process the transmitted signals and compare the processed transmitted signals with stored or accessed (locally or distally) image data of acceptable backs of playing cards identical to the backs of the playing cards being used; and
e) identifying degrees of difference between the processed transmitted signals and the stored or accessed image data which is indicative of an unacceptable difference or a visually meaningful difference between the image on the back of playing cards.

Such meaningful differences may be any one of size of elements on the image, spacing or elements on the image, surface area variations on the card (as where a card has been cut or abraded at an edge), additional image content, absence of image content, angularity of image content, shape of image content, and even color of image content.

The surface in the system preferably comprises a playing card, with a back surface of the playing card without (intentional) suit and rank information printed thereon. By lack of intent is meant that an "honest" card is used where the backs and sides of the individual cards are intended to be indistinguishable from one another. There may be fraudulent or illegal markings or printing defects that can distinguish between cards and provide or suggest face values, suits and/or ranks of the playing cards. It is an aspect of the present technology to detect such fraudulent, criminal or accidental face (value, suit and/or rank) identifying markings on the back side of the playing cards. In some cases, the printing errors may be as subtle as smears, disorientations, poor ink transfers, misalignment, lack of color registration, or ink bleed (horizontal or through the thickness of the cards). These honest defects are still sources of player advantage outside the scope of the rules of game play and would be used by a player seeking an advantage, whether that player believes the use is ethical or not.

Spurious or intentional markings can be the result of fraudulently intended transfer of markings of any sort to give a player an advantage. The markings may be subtle visible markings (as an obvious marking would be seen by all and call attention to the fact that there has been marking) such as minute cuts on edges (which might be more easily felt than seen), infrared radiation reflecting inks or pigments, ultraviolet radiation reflecting inks or pigments, surface abrading steps that can alter the radiation reflecting properties of the back surface of the playing card, and any other marking that can be visually detected. The visual detection is unlikely to be enhanced or enabled by lenses or glasses that attempt to aid in the reading of the otherwise invisible inks. As the player that has marked the cards will be reading through glasses from the reflection of truly ambient radiation and not intentionally projected radiation (it would be difficult to provide projected radiation unless there were cooperation from the casino or structure where the card game was being played) and as the casino radiation is outside visible ranges (unless military style infrared sensing systems were used, which would be blatantly obvious in a casino environment).

By providing a potentially full range of spectral illumination (infrared, ultraviolet and even additional visible white light illumination) on the backs of the playing cards, detection of all forms of image marking is enabled. As players who are seeking information from such markings will typically have to use only the available background radiation for viewing (since a player shining a light onto the playing cards would be easily detected), the use of additional casino controlled projection of radiation enables greater image content and intensity availability for security purposes in detecting flaws and markings. Reflected radiation is collected by a sensor positioned to be within a range of reflected radiation from the surface of playing cards. Using standard software for image capture (as known in the art cited herein), the collected radiation is converted to image data which is transmitted to an image display system to create the displayed image. This transformation of the raw received radiation could be performed by local logic (e.g., field programmable gated arrays, ASICs, chip boards and the like) or by a dedicated or local processor in communication with the system. In one simple embodiment, a single box or housing (usually with a top, bottom, two sides and a back, with the front open to allow insertion of the playing cards, as in FIG. 1) may have multiple infrared emitters (LEDs, lasers, bulbs, semiconductors, etc.), multiple ultraviolet radiation emitters (LEDs, bulbs, semiconductors, lasers, etc.) and even white visible light emitters within the housing direct the radiation at an area on the bottom of the box where one or more playing cards can be placed, backside (no card symbols shown) facing upwards. The sensors would be placed at a location (e.g., facing downward from the inside top of the housing) to most efficiently collect the reflected radiation. The sensor or camera should extend to a position at least as low as the lowest emitter, and preferably lower than the lowest emitter so as to minimize direct transmission of the radiation from the emitters to the sensor, without reflection. There should be at least two emitters for each of the infrared and ultraviolet portions of the spectrum to assure broad coverage of the surface of the playing cards, even though a single emitter for each portion of the spectrum would work. For the infrared, the spectral range may, by way of non-limiting examples, be within 780-1100 nm, the ultraviolet may be within 280-410 nm and the like. There may be 1, 2, 3, 4, 5, 6 or more emitters for each spectral range, as the power consumption for each wavelength can be quite small. The low power consumption would allow for portable battery powered units as well as power cord plug-in units.

FIG. 1 shows a full frontal view of a box construction 2 for the system. This box construction 2 could also be sized to be a section within a delivery shoe or playing card shuffler (neither shown). The box construction 2 has a top 4, A BOTTOM 6, A LEFT SIDE 8 AND A RIGHT SIDE 10. One or more playing cards 12a and 12b may lie on the bottom 6 of the box construction 2. A series of infrared emitters (triangles 14) and ultraviolet emitters (squares 16) are shown distributed along the lower inside surface of the top 4. A camera/sensor box (with sensing capability matching or including the output of emitters 14 and 16) extends below the farthest extension of the emitters 14 and 16. A signal conducting system (20) such as wires, plates, panels and the like carries signals between components. An I/O port to carry signals to a processor or logic system (not shown) is in communication with the signal conducting system (20).

The original signals (reflected radiation) captured by the sensors is then converted to data that can be displayed (or even just analyzed by a processor configured with software). An aspect of the technology can be to merely display an image of the back of the playing card(s) so that markings can be visually inspected for, or to have the captured image of the back of the card visually or processor compared with a stored image of the back of that format of playing card. These stored images can either be within a look-up table of a large number of playing cards in the processor or accessed from a distal library for the specific cards used), or one or more images (to provide a standard image) can be made of the backs of playing cards at the beginning of a session to create an comparison image for that card set. A "standard" image of the back of playing cards can be important where manufacturing defects might be present. Slight rotations of the printed images, smears, discolorations, poor inking and the like can be as effective readable markings for individual playing cards as intentionally applied markings or daubs.

Edge markings and edge cuts can also be detected by software looking for variations in the linearity of sides or edges of playing cards. Surface abrasions of the backs of the cards (which would not require ink or pigments applied) would alter the reflection characteristics in areas of the cards which could be visually or tactilely detected (with or without a player using artificial means) and could be detected by software looking for deviations in ideal reflection off the backs of the playing cards.

Software is available or can be easily constructed by ordinary skill that allows comparison of the scanned image and the detailed image. Even the software of the incorporated U.S. Pat. No. 8,119,975 (which fits overlapping elements of scanned data into a single, uniform and meaningful image) could be easily modified to compare images as well as identify degrees of differences between the scanned and reference image that rises to the level of potentially or actually visible differences.

The system my further have: an ambient ultraviolet radiation source for directing ultraviolet radiation at the surface; an ultraviolet radiation sensor for capturing reflected ambient ultraviolet radiation; the ultraviolet radiation sensor configured to transmit signals based on captured reflected ultraviolet radiation; the transmitted signals from the ultraviolet radiation symbol providing data that contains ultraviolet image data reflected off of the surface; a processor configured to receive the transmitted signals from the reflected ultraviolet radiation, process the transmitted signals from the reflected ultraviolet radiation and transmit the processed transmitted signals from the reflected ultraviolet radiation in a format that can be displayed on a display system; and a display system configured to display an image of the surface from which ultraviolet radiation was reflected based on the infrared image data and the ultraviolet radiation data. Again, the infrared radiation source is pulsed to reduce heating of the surface by infrared radiation. The infrared radiation source may be configured to pulse the infrared radiation contemporaneously with the emitting of ultraviolet radiation by the ultraviolet radiation source. The processor may be configured to combine the infrared radiation signals and the ultraviolet radiation signals to form a composite image on the display system. The processor may be configured to compare that transmitted signals with reference data of a standard playing card back. The processor may be configured to i) compare the transmitted signals comprising image data of the back of a playing card based on reflected data and reference data stored in memory of a standard playing card back surface and ii) identify differences between the transmitted signals comprising image data of the back of a playing card based on reflected data and reference data stored in memory and the processor then is configured to provide image data of the comparison to either a) highlighted in a visual display or b) the processor identifying a degree of difference between the image of the back of the playing card based on the image data and the reference data, and the processor may be configured to determine a degree of difference between the image of the back of the playing card based on the image data and the reference data is identified in b) by an alphanumeric rating, color rating or symbolic rating. Again, the infrared sensor may be located at a position elevated above a surface of the gaming table, especially where the sensor is at a position elevated to a height wherein infrared radiation reflected from the back surface of the playing card at an angle of between 60 and 90 degrees (a broader range of 30 to 90 degrees can work, but it creates a possibility of reduced quality images, especially where multiple sources of emitted radiation are used, and reflections may come to sensors from multiple emitting sources) from horizontal is received by the sensor. The processor may be configured to i) compare the combined transmitted signals comprising image data of the back of a playing card based on reflected data and reference data stored in memory of a standard playing card back surface and ii) identify differences between the combined transmitted signals comprising image data of the back of a playing card based on reflected data and reference data stored in memory and the processor then is configured to provide image data of the comparison to either a) highlighted in a visual display or b) the processor identifying a degree of difference between the image of the back of the playing card based on the image data and the reference data, and again the processor may be configured to determine a degree of difference between the image of the back of the playing card based on the image data and the reference data is identified in b) by an alphanumeric rating, color rating or symbolic rating. The infrared sensor is located at a position elevated above a surface of the gaming table, such as where the surface is provided within a housing comprising a bottom, a top, a back and two sides, and the ambient source of infrared radiation is provided by at least two infrared emitters on the top, back and/or two sides, and the infrared sensor is supported on the top. The surface may be provided within a housing comprising a bottom, a top, a back and two sides, and the ambient source of infrared radiation is provided by at least two infrared emitters on the top, back and/or two sides, and the ambient source of ultraviolet radiation is provided by at least two ultraviolet emitters on the top, back and/or two sides, and the infrared sensor and the ultraviolet sensor are supported on the top. The housing may include a card support for a set of playing cards, and a moving system for moving individual playing cards from the card support to the surface so that a back of the playing card is exposed to the transmitted infrared radiation and infrared radiation is reflected from the back of the playing card. This housing may be a mechanical or manual shoe, a shuffling or randomization system.

It is also to be noted that the system of the present technology may be used to verify other gaming objects to prevent fraudulent substitution of gaming objects. Invisible dyes (again IR or UV visible) can be embedded in or painted on (with readable codes), and the system can be used to verify the chips based on reading the applied code. To prevent duplication of the code by third parties, the code can be altered easily by regular removal (a simple wash) and reapplication of the invisible code. Chips may be easily coated on a regular basis, but die would usually have to have the ink or pigment embedded within the structure to be viewed by the system technology, with UV and/or IR radiation and reflection. This system enables more secure and faster verification of dice then the standard visual inspection. The identical system, with only software varied to address dice image or chip image content can be used.

FIG. 4 shows a perspective view of an alternative device 400 according to the present technology. The inspection device 400 is shown in an alternative embodiment with a base 402 a top 404 and a side 406. In the middle of the top 404 is a display monitor 408 on the top 404 which extends through the top 404 into an open volume 418 and is in association with a 416 camera/processor combination 416. The camera/processor combination 416 has potential and/or selective sensitivity to visible light, infrared radiation and/or ultraviolet radiation. This radiation and light is simultaneously or separately provided (according to design or control) from visible light emitter 410, ultraviolet radiation emitter 412 and infrared radiation emitter 414, which radiation is reflected off cards 420 (here the back of cards, but fronts of cards may also be used) and captured by the camera/processor 416 combination. The camera segment receives the reflected radiation and the processor converts it into displayable image content for the display monitor 408. Separate components may be alternatively used.

As noted, the at least three ranges of radiation sensed by the camera/processor combination 416 may be used contemporaneously, in sub-combination or sequentially and separately. A control panel of power button 422, infrared radiation control 424, ultraviolet radiation control 426 and visible light control 428 are shown on the side 406. A default operation in the processor may allow for all three emissions to occur simultaneously upon turning power on with power button 422, and the other three controls 424, 426 and 426 may be used to turn off radiation emitters as desired. Alternatively, individual ones of the three controls 424, 426 and 426 may be used to initiate individual, combination, sequential or contemporaneous emissions.

The system may screen for defects from all wavelengths at one time, and then individual radiation images may be used or just individual images from each radiation emission, reflection and capture may be used. The processor may store images for programmed time periods, or when one of the three controls 424, 426 and 426 is depressed, and image of reflection from that image may be captured by the processor and stored in memory. The individual images can be displayed and visually evaluated and/or the processor may compare the displayed image (data) content with standardized image data to determine if there are spurious markings on the back of the cards.

In scanning or imaging backs of playing cards, the fraudulent markings can be present at any discernible wavelength within the electromagnetic spectrum. Although visible wavelengths are an amateurish method of marking cards as they can be seen equally by any person at the game table, especially anyone using filters that assist in limiting viewable radiation to the wavelengths in which the fraudulent markings have been made. Although the visible markings are the easiest to observe and therefore the most difficult wavelengths with which to commit fraud, it is still desirable to offer protection against those wavelengths in the technology of the present invention.

The enhanced ability to see visible, near UV, and near IR wavelengths can be easily enhanced on hand-held and eye-in-the-sky visual systems by the provision of appropriate radiation filters between the surfaces to be viewed (e.g., the back of playing cards) and the viewing lens, such as the lens on a hand-held phone, smartphone, iPad, tablet or the like. The filters may be strategically positioned at intervals (e.g., putting all filters in place simultaneously would merely filter out all radiation blocked by the filters) to provide apparently enhanced images at specific wavelengths. The sequential use of filters at the differing wavelength ranges (e.g., UV from 280-410, various segments of the visible range between 410 and 700 (with filters selected for individual ranges such as violet, indigo, blue, green, yellow, orange and red), and various segments of the infrared, such as 700-780 for the near infrared and 780-900 for the mid IR, and 900-1050 or up to 1200 for the farther infrared. Appropriately placing each of the filters, one-at-a-time between the surface to be viewed and the lens gives a relatively false impression of enhanced security, which provides more of an impression of efficacy rather than the significant advantage provided by using various UV filters and various IR filters according to the present technology.

It is important to note that the greatest benefit in the use of filters is enabling broad spectrum sensors (such as camera sensors, that have a natural or built-in sensitivity to non-visible spectra (e.g., UV and IR) to cut out visible spectra to enhance the contrast of images (e.g., fraudulently applied images) and background in the non-visible spectra so that the enhanced contrast images can be displayed as visible images on a display screen. The non-visible image content is displayed a an artificially selected visible color or as black-and-white for the display.

The switching of lenses or filters with only visible spectrum capability may give an appearance of broad screening functionality, but is minimally effective in screening for fraud, because the markings are already in the visible spectrum and can be seen by the naked eye, even with some difficulty. It is the use of cut-off filters that eliminate regions of or the entire visible spectrum that enables effective viewing of fraudulent markings in the UV and IR by the systems in the present technology.

This is especially true with the hand-held devices such as phone cameras, pad cameras and tablet cameras. A brief understanding of the nature of filters will assist in understanding how these components work, and how they may operate in the practice of the present technology.

Optical filters are devices that selectively transmit light of different wavelengths, usually implemented as plane glass or plastic devices in the optical path which are either dyed in the bulk or have interference coatings. Optical filters are completely described by their frequency response, which specifies how the magnitude and phase of each frequency component of an incoming signal is modified by the filter.

Filters mostly belong to one of two categories. The simplest, physically, is the absorptive filter; interference or dichroic filters can be quite complex.

Optical filters selectively transmit light in a particular range of wavelengths, that is, colors, while blocking the remainder. They can usually pass long wavelengths only (longpass), short wavelengths only (shortpass), or a band of wavelengths, blocking both longer and shorter wavelengths (bandpass). The passband may be narrower or wider; the transition or cutoff between maximal and minimal transmission can be sharp or gradual. There are filters with more complex transmission characteristic, for example with two peaks rather than a single band;[2] these are more usually older designs traditionally used for photography; filters with more regular characteristics are used for scientific and technical work.

Optical filters are commonly used in photography (where some special effect filters are occasionally used as well as absorptive filters), in many optical instruments, and to color stage lighting. In astronomy optical filters are used to restrict light passed to the spectral band of interest, e.g., to study infrared radiation without visible light which would affect film or sensors and overwhelm the desired infrared.

Photographic filters are a particular case of optical filters, and much of the material here applies. Photographic filters do not need the accurately controlled optical properties and precisely defined transmission curves of filters designed for scientific work, and sell in larger quantities at correspondingly lower prices than many laboratory filters. Some photographic effect filters, such as star effect filters, are not relevant to scientific work.

Absorptive filters are usually made from glass to which various inorganic or organic compounds have been added. These compounds absorb some wavelengths of light while transmitting others. The compounds can also be added to plastic (often polycarbonate or acrylic) to produce gel filters, which are lighter and cheaper than glass-based filters.

Alternately, dichroic filters (also called "reflective" or "thin film" or "interference" filters) can be made by coating a glass substrate with a series of optical coatings. Dichroic filters usually reflect the unwanted portion of the light and transmit the remainder.

Dichroic filters use the principle of interference. Their layers form a sequential series of reflective cavities that resonate with the desired wavelengths. Other wavelengths destructively cancel or reflect as the peaks and troughs of the waves overlap.

Dichroic filters are particularly suited for precise scientific work, since their exact color range can be controlled by the thickness and sequence of the coatings. They are usually much more expensive and delicate than absorption filters.

The basic scientific instrument of this type is a Fabry-Perot Interferometer. It uses two mirrors to establish a resonating cavity. It passes wavelengths that are a multiple of the cavity's resonance frequency.

Monochromatic filters only allow a narrow range of wavelengths (essentially a single color) to pass.

The term "infrared filter" can be ambiguous, as it may be applied to filters to pass infrared (blocking other wavelengths) or to block infrared (only). Infrared-passing filters are used to block visible light but pass infrared; they are used, for example, in infrared photography. Infrared cut-off filters are designed to block or reflect infrared wavelengths but pass visible light. Mid-infrared filters are often used as heat-absorbing filters in devices with bright incandescent light bulbs (such as slide and overhead projectors) to prevent unwanted heating due to infrared radiation. There are also filters which are used in solid state video cameras to block IR due to the high sensitivity of many camera sensors to unwanted near-infrared light.

Ultraviolet (UV) filters block ultraviolet radiation, but let visible light through. Because photographic film and digital sensors are sensitive to ultraviolet (which is abundant in skylight) but the human eye is not, such light would, if not filtered out, make photographs look different from the scene visible to people, for example making images of distant mountains appear unnaturally hazy. An ultraviolet-blocking filter renders images closer to the visual appearance of the scene.

As with infrared filters there is a potential ambiguity between UV-blocking and UV-passing filters; the latter are much less common, and more usually known explicitly as UV pass filters and UV bandpass filters.

Neutral density (ND) filters have a constant attenuation across the range of visible wavelengths, and are used to reduce the intensity of light by reflecting or absorbing a portion of it. They are specified by the optical density (OD) of the filter, which is the negative of the common logarithm of the transmission coefficient. They are useful for making photographic exposures longer.

A longpass (LP) Filter is an optical interference or colored glass filter that attenuates shorter wavelengths and transmits (passes) longer wavelengths over the active range of the target spectrum (ultraviolet, visible, or infrared). Longpass filters, which can have a very sharp slope (referred to as edge filters), are described by the cut-on wavelength at 50 percent of peak transmission. In fluorescence microscopy, longpass filters are frequently utilized in dichroic mirrors and barrier (emission) filters.

Bandpass filters only transmit a certain wavelength band, and block others. The width of such a filter is expressed in the wavelength range it lets through and can be anything from much less than an Angstrom to a few hundred nanometers. Such a filter can be made by combining an LP- and an SP filter.

A shortpass (SP) Filter is an optical interference or colored glass filter that attenuates longer wavelengths and transmits (passes) shorter wavelengths over the active range of the target spectrum (usually the ultraviolet and visible region). In fluorescence microscopy, shortpass filters are frequently employed in dichromatic mirrors and excitation filters.

The filters, especially the cut-off filters to reduce or eliminate specific wavelengths and/or ranges of wavelengths transmitted through the filters, including substantially most or all of the visible spectrum, while allowing most or all of the non-visible spectrum or ranges of the non-visible spectrum, such as most or all wavelengths above 700 nm, and/or below 400 nm, is one potential use of the filters. The filters are placed in a position where radiation reflected off of or transmitted through the backs of the playing cards pass into and through the filter and then to a sensor, such as a hand-held camera on a phone, tablet or pad.

The filter may be positioned by manually holding a filter in that position, mechanically supporting the filter in that position, laying the filter on the playing card or attaching the filter to the sensor or the housing supporting the sensor.

The filters may be independently structured (e.g., a box of 3, 4, 5, 6, 7, 8, 9 or 10 filters for example), the filters may be in a fan attachment as is done with paint samples (e.g., a corner of each filter is secured to a common post or chain, so that individual filters can remain in order as each filter is positioned), or the filters may be in a structure where filters are individually snapped or slid or rotated into position between the reflected image and the sensor.

Figure 5:
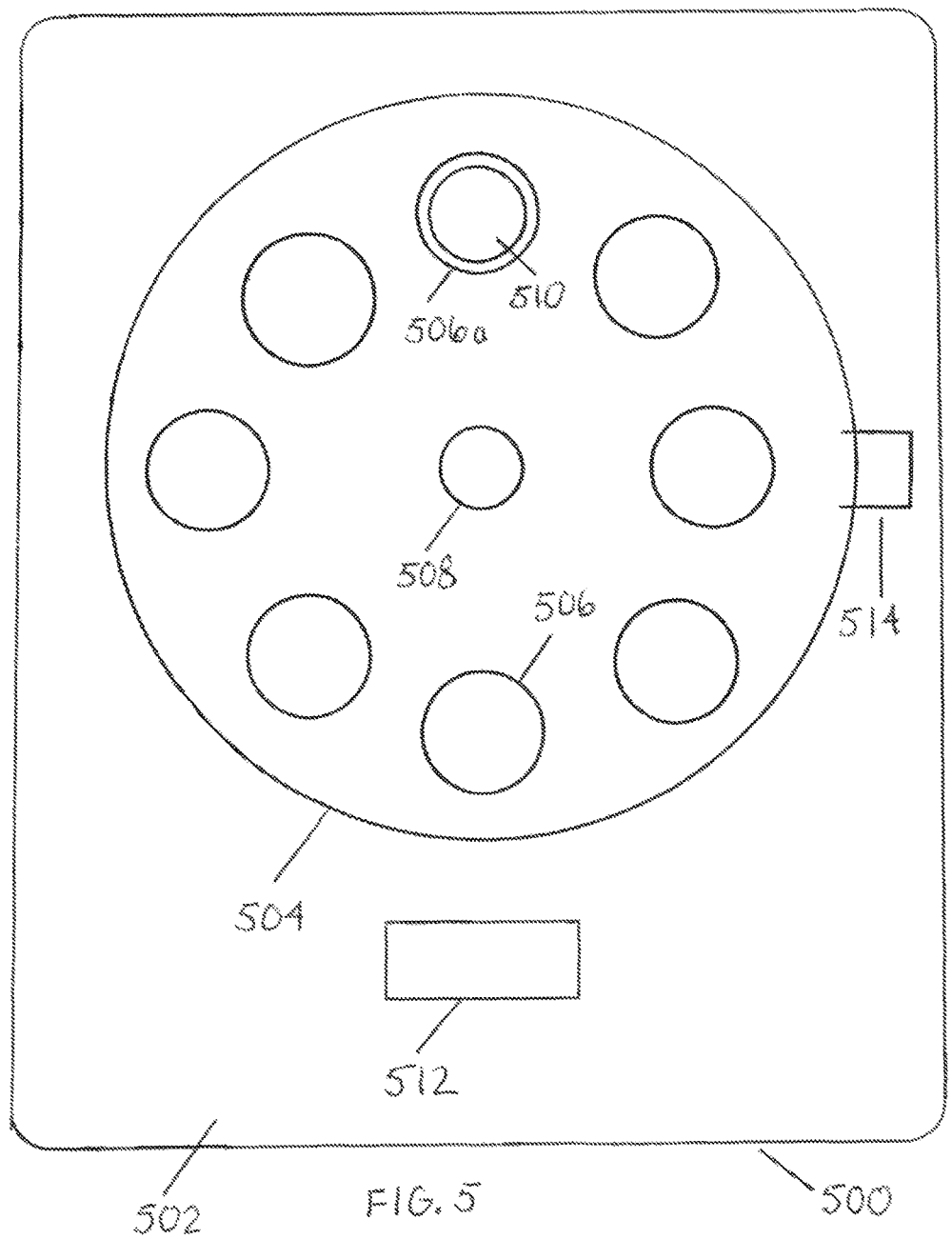
FIG. 5 shows a front view of a hand-held, multi-filter device according to the present technology.

FIG. 5 shows an example of a hand-held device 500 with a collection of filters 506 that may be used in the practice of the present technology. The device 500 has a frame 502 that supports a wheel 504 carrying (by way of non-limiting example) eight separate cut-off filters 506. The wheel spins or snaps about a central axial support 508 securing the wheel 508 to the housing 502. A finger drive 514 may be used to rotate or snap the wheel 5041 into positions where individual filters (e.g., 506a) can be positioned over the see-through hole 510 which is positioned to receive and transmit reflected or transmitted radiation from playing cards (not shown). The wavelength of each individual filter (e.g., 506a) in position over the through-hole 510 may be identified in a responsive display panel 512.

A structure similar to that, or more simple than, the device 500 may be physically attached, e.g., slid or snapped into place, on a phone, pad or tablet or other hand-held sensor with a camera function.

The hand-held device may be a hand-held device for detecting errors in the back of playing cards in which there are: a) a radiation sensor for capturing ambient radiation; the radiation sensor configured to transmit signals based on captured radiation; the transmitted signals providing data that contains image data of the captured radiation with both visible wavelength radiation and radiation outside the visible wavelengths; b) a processor configured to receive the transmitted signals as both visible wavelength radiation and radiation outside the visible wavelengths, process the transmitted signals both visible wavelength radiation and radiation outside the visible wavelengths and transmit the processed transmitted signals in a format that can be displayed as a visible image on c) a display system combining the processed transmitted data into the visible image; and
the display system being configured to display the visible image of a surface from which both visible radiation and radiation outside the visible wavelengths was reflected off or transmitted through to provide the transmitted signals;
wherein d) a cut-off filter allowing transmission of radiation outside of the visible spectrum is positioned between the radiation sensor and the back of a playing card. The sensor should be sensitive to radiation within a range including ultraviolet wavelengths, visible wavelengths and infrared wavelengths. The hand-held device may have a single sensor which is sensitive to radiation within a range including at least a 50 nm range within each of ultraviolet wavelengths, visible wavelengths and infrared wavelengths.

The hand-held device preferably includes associated therewith a set of cut-off filters, the set of cut-off filters comprising at least one filter that reduces transmission in a 100 nm range within the visible region of the electromagnetic spectrum by at least 50% and transmits at least 75% of infrared radiation between a 100 nm range in the infrared between 750 and 1200 nm. The individual filters may be positioned between the image source and the sensor (e.g., over a transmission lens) to receive and appropriately filter the image radiation. The set of cut-off filters, the set of cut-off filters comprising at least one filter that reduces transmission in a 100 nm range within the visible region of the electromagnetic spectrum by at least 50% and transmits at least 75% of infrared radiation between 750 and 850 nm.

The hand-held system may also include LED lights to improve the amount of radiation reflected off the backs of playing cards. The particular wavelength of the combined LEDs may extend over the entire desired range of viewing reflections, or individual LEDs having wavelengths of emission overlapping the range of transmission of the individual filters may be used. Thus at least three LED emitters may be used, one UV, one visible and one IR (used simultaneously or independently), or multiple LEDs covering ranges more particularly consistent with the individual filters may be used. For example, with the device of FIG. 5, there may be 3, 4, 5, 6, 7 or 8 LED emitters to assure appropriate emissions in the transmission or cut-off wavelengths desired to be used with the filters.

The system may also be used in a parallel "eye-in-the-sky" system, with the sensor(s) being in domes in elevated positions, such as on the ceilings, and the filters being automatically, mechanically interchangeable by an operator surveying the table tops as is done to inspect for fraud at gaming tables. The infrared scanning capability may have an additional benefit as infrared emissions from playing cards or even dice that have been hidden by the player and brought onto the table would register at a higher temperature (measured by infrared emissions) than cards being on the gaming tables in the air-conditioned environment of the casino or card room.

The eye-in-the-sky, having greater potential for access to significant computing power may also be associated with software that can automatically identifying a degree of false marking on playing cards and automatically indicate the potential for fraud, without primary human intervention in attempting to read the backs of playing cards.

The devices of the present technology may be further constructed as wherein the set of cut-off filters are attached to the hand-held device so that individual ones or multiple ones of the cut-off filters can be positioned between the surface from which both visible radiation and radiation outside the visible wavelengths is transmitted and the radiation sensor. Attachment of the cut-off filters to the hand-held device may allow rotation of at least one cut-off filter into a position between the surface from which both visible radiation and radiation outside the visible wavelengths is transmitted and the radiation sensor. The hand-held device may have the set of cut-off filters attached to the hand-held device so that individual ones or multiple ones of the cut-off filters can be positioned between the surface from which both visible radiation and radiation outside the visible wavelengths is transmitted and the radiation sensor. Attachment of the cut-off filters to the hand-held device may allow rotation of at least one cut-off filter into a position between the surface from which both visible radiation and radiation outside the visible wavelengths is transmitted and the radiation sensor. The cut-off filters may rotate individually (each filter having its own rotation point through a pin or the like) or rotate in unison within a plate holding multiple filters.

Although specific structures, components, materials, dimensions and parameters have been described to assure enablement of the invention, those are merely specific examples within the generic concepts of the present invention and should not be read as limiting the scope of the invention as claimed.

What is claimed:

1. A hand-held device for detecting errors or fraudulent markings on the back of playing cards comprising:
   a radiation sensor for capturing ambient radiation;
   the radiation sensor configured to transmit signals based on captured radiation;
   the transmitted signals providing data that contains image data of the captured radiation with both visible wavelength radiation and radiation outside the visible wavelengths;

a processor configured to receive the transmitted signals as both visible wavelength radiation and radiation outside the visible wavelengths, process the transmitted signals both visible wavelength radiation and radiation outside the visible wavelengths and transmit the processed transmitted signals in a format that can be displayed as a visible image on a display system combining the processed transmitted data into the visible image; and the display system configured to display the visible image of a surface from which both visible radiation and radiation outside the visible wavelengths were reflected off or transmitted through to provide the transmitted signals;

wherein a cut-off filter allowing transmission of radiation outside of the visible spectrum is positioned between the radiation sensor and the back of a playing card.

2. The hand-held device of claim 1 wherein the sensor is sensitive to radiation within a range including at least 100 nm ranges within each of ultraviolet wavelengths, visible wavelengths and infrared wavelengths.

3. The hand-held device of claim 1 wherein there is a single sensor is sensitive to radiation within a range including at least 50 nm ranges within each of ultraviolet wavelengths, visible wavelengths and infrared wavelengths.

4. The hand-held device of claim 2 wherein there is a single sensor is sensitive to radiation within a range including at least 50 nm ranges within each of ultraviolet wavelengths, visible wavelengths and infrared wavelengths.

5. The hand-held device of claim 1 wherein the hand-held device comprises a set of cut-off filters, the set of cut-off filters comprising at least one filter that reduces transmission in a 100 nm range within the visible region of the electromagnetic spectrum by at least 50% and transmits at least 75% of infrared radiation between a 100 nm range in the infrared between 750 and 1200 nm.

6. The hand-held device of claim 1 wherein the hand-held device comprises a set of cut-off filters, the set of cut-off filters comprising at least one filter that reduces transmission in a 100 nm range within the visible region of the electromagnetic spectrum by at least 50% and transmits at least 75% of infrared radiation between 750 and 850 nm.

7. The hand-held device of claim 5 wherein the set of cut-off filters are attached to the hand-held device so that individual ones or multiple ones of the cut-off filters can be positioned between the surface from which both visible radiation and radiation outside the visible wavelengths is transmitted and the radiation sensor.

8. The hand-held device of claim 7 wherein attachment of the cut-off filters to the hand-held device allows rotation of at least one cut-off filter into a position between the surface from which both visible radiation and radiation outside the visible wavelengths is transmitted and the radiation sensor.

9. The hand-held device of claim 6 wherein the set of cut-off filters are attached to the hand-held device so that individual ones or multiple ones of the cut-off filters can be positioned between the surface from which both visible radiation and radiation outside the visible wavelengths is transmitted and the radiation sensor.

10. The hand-held device of claim 9 wherein attachment of the cut-off filters to the hand-held device allows rotation of at least one cut-off filter into a position between the surface from which both visible radiation and radiation outside the visible wavelengths is transmitted and the radiation sensor.

11. The hand-held device of claim 8 wherein the cut-off filters rotate individually or rotate in unison within a plate holding multiple filters.

12. The hand-held device of claim 9 wherein the cut-off filters rotate individually or rotate in unison within a plate holding multiple filters.

13. An eye-in-the-sky security device for detecting errors in the back of playing cards comprising a housing:

the housing including a radiation sensor for capturing ambient radiation;

the radiation sensor configured to transmit signals based on captured radiation;

the transmitted signals providing data that contains image data of the captured radiation with both visible wavelength radiation and radiation outside the visible wavelengths;

a processor configured to receive the transmitted signals as both visible wavelength radiation and radiation outside the visible wavelengths, process the transmitted signals both visible wavelength radiation and radiation outside the visible wavelengths and transmit the processed transmitted signals in a format that can be displayed as a visible image on a display system combining the processed transmitted data into the visible image; and the display system configured to display the visible image of a surface from which both visible radiation and radiation outside the visible wavelengths was reflected off or transmitted through to provide the transmitted signals;

wherein a cut-off filter allowing transmission of radiation outside of the visible spectrum is positioned between the radiation sensor and the back of a playing card.

14. The eye-in-the-sky security device of claim 13 wherein the radiation sensor is sensitive to radiation within a range including at least 100 nm ranges within each of ultraviolet wavelengths, visible wavelengths and infrared wavelengths.

15. The eye-in-the-sky security device of claim 13 wherein there is a single sensor is sensitive to radiation within a range including at least 50 nm ranges within each of ultraviolet wavelengths, visible wavelengths and infrared wavelengths.

16. The eye-in-the-sky security device of claim 14 wherein there is a single sensor that is sensitive to radiation within a range including at least 50 nm ranges within each of ultraviolet wavelengths, visible wavelengths and infrared wavelengths.

17. The eye-in-the-sky security device of claim 13 wherein the hand-held device comprises a set of cut-off filters, the set of cut-off filters comprising at least one filter that reduces transmission in a 100 nm range within the visible region of the electromagnetic spectrum by at least 50% and transmits at least 75% of infrared radiation between a 100 nm range in the infrared between 750 and 1200 nm.

18. The hand-held device of claim 17 wherein the set of cut-off filters are attached to the hand-held device so that individual ones or multiple ones of the cut-off filters can be positioned between the surface from which both visible radiation and radiation outside the visible wavelengths is transmitted and the radiation sensor.

19. The hand-held device of claim 18 wherein attachment of the cut-off filters to the hand-held device allows rotation of at least one cut-off filter into a position between the surface from which both visible radiation and radiation outside the visible wavelengths is transmitted and the radiation sensor.

20. The hand-held device of claim 19 wherein the cut-off filters rotate individually or rotate in unison within a plate holding multiple filters.

\* \* \* \* \*